United States Patent [19]

Westerman

[11] Patent Number: 4,751,057
[45] Date of Patent: Jun. 14, 1988

[54] CATALYTIC CONVERSION OF GAS OR LIQUID IN A MILTITUBE REACTOR

[75] Inventor: David W. B. Westerman, Amsterdam, Netherlands

[73] Assignee: Shell Oil Company, Houston, Tex.

[21] Appl. No.: 861,953

[22] Filed: May 12, 1986

[30] Foreign Application Priority Data

Jul. 2, 1985 [GB] United Kingdom ............... 8516673

[51] Int. Cl.⁴ .............................................. B01J 8/06
[52] U.S. Cl. ................. 422/197; 261/114.5; 422/220; 422/312
[58] Field of Search ............ 422/193, 195, 196, 197, 422/220, 312; 261/114.5

[56] References Cited

U.S. PATENT DOCUMENTS

| | | | |
|---|---|---|---|
| 2,139,943 | 12/1938 | Fenske et al. | 422/197 |
| 2,395,777 | 2/1946 | Brunjes et al. | 422/197 |
| 2,986,454 | 5/1961 | Jewett | 422/197 |
| 3,006,740 | 10/1961 | Maggio | 422/220 |
| 3,230,055 | 1/1966 | Wolfrom | 422/197 |
| 3,440,018 | 4/1969 | Eckert | 422/220 |
| 3,524,731 | 8/1970 | Effron et al. | 422/220 |
| 3,532,472 | 10/1970 | Foster | 422/197 |
| 3,918,917 | 11/1975 | Ashina et al. | 422/197 |
| 4,126,540 | 11/1978 | Grosboll et al. | 208/146 |
| 4,173,615 | 11/1979 | Otsuka et al. | 422/197 |
| 4,187,897 | 1/1980 | Lanteri | 422/197 |

FOREIGN PATENT DOCUMENTS

| | | |
|---|---|---|
| 163357 | 4/1985 | European Pat. Off. |
| 2516125 | 4/1975 | Fed. Rep. of Germany |
| 976036 | 11/1964 | United Kingdom |

Primary Examiner—Michael S. Marcus

[57] ABSTRACT

In a multitube reactor gas and liquid are allowed to pass through reactor tubes, effluents are removed from the lower ends of the reactor tubes, and heat-exchange fluid is passed along the outer surfaces of the reactor tubes. To obtain a uniform distribution of liquid to the upper ends of the reactor tubes, the liquid is supplied to a plurality of adjacent trays which are in fluid communication with the reactor tubes.

7 Claims, 3 Drawing Sheets

CATALYTIC CONVERSION OF GAS OR LIQUID IN A MILTITUBE REACTOR

FIELD OF THE INVENTION

The invention relates to a process for the catalytic conversion of a gas or a liquid in a multitube reactor comprising a plurality of substantially vertical reactor tubes filled with catalyst particles.

BACKGROUND OF THE INVENTION

An example of such a process of the present invention is the catalytic conversion of synthesis gas, comprising carbon monoxide and hydrogen, into middle distillates. In this process synthesis gas is supplied to the upper ends of the reactor tubes, passed through the reactor tubes and the effluents are collected downstream of the lower ends of the reactor tubes. To distribute the heat of reaction generated during the catalytic conversion uniformly over the cross-sections of the reactor tubes, and to improve heat-transfer from the interiors of the reactor tubes to the inner surfaces of the walls of said tubes a heat-transfer liquid is introduced into the upper ends of the reactor tubes. The heat of reaction is removed from the reactor tubes by a heat-transfer fluid which is passed along the outer surfaces of the said tubes.

In catalytic conversion processes use is made of multitube reactors having a diameter of about 5 m and comprising in the range of from about 5,000 reactor tubes with a diameter of about 45 mm to about 15,000 reactor tubes with a diameter of about 25 mm.

Such a large multitube reactor cannot be constructed in such a manner that it extends exactly vertically and small deviations from the vertical of about 1 cm per 800 cm are common.

It is an object of the present invention to provide a process for the catalytic conversion of a gas or a liquid in a multitube reactor having a plurality of substantially vertical reactor tubes wherein equal amounts of liquid are supplied to the reactor tubes to prevent overheating of one or more reactor tubes. British Pat. No. 976,036 discloses a reactor provided with a number of horizontal trays for liquid distribution, however, this patent does not relate to a multitube reactor as in the invention of this application.

SUMMARY OF THE INVENTION

This invention describes a process for the catalytic conversion of a gas or a liquid in a multitube reactor having a plurality of substantially vertical reactor tubes filled with catalyst particles which process comprises supplying gas to the upper ends of the reactor tubes, supplying liquid to a plurality of adjacent, substantially horizontal trays which are in communication with the upper ends of the reactor tubes, allowing the liquid to enter the upper ends of the reactor tubes, passing the gas and the liquid through the reactor tubes, collecting the effluents leaving the lower ends of the reactor tubes, and passing heat-exchange fluid along the outer surfaces of the reactor tubes.

In addition, the invention describes and apparatus for performing a process for catalytic conversion in a multitube reactor, which reactor comprises a normally substantially vertically extending vessel, a plurality of reactor tubes arranged in the vessel substantially parallel to its central longitudinal axis of which the upper ends are fixed to an upper tube plate and in communication with a fluid inlet chamber above the upper tube plate and of which the lower ends are fixed to a lower tube plate and in fluid communication with an effluent collecting chamber below the lower plate, a means for passing heat-exchange fluid along the outer surfaces of the reactor tubes, an effluent outlet arranged in the effluent collecting chamber, a gas inlet arranged in the fluid inlet chamber, a liquid distributor in the fluid inlet chamber which includes a plurality of adjacent, substantially horizontal trays which are in fluid communication with the upper ends of the reactor tubes, and a liquid supply means for supplying liquid to the trays.

DETAILED DESCRIPTION OF THE INVENTION

The invention will now be described in more detail by way of example with reference to the drawings, wherein FIG. 1 shows a partly longitudinal section of a multitube reactor according to the invention;

Figure 1:
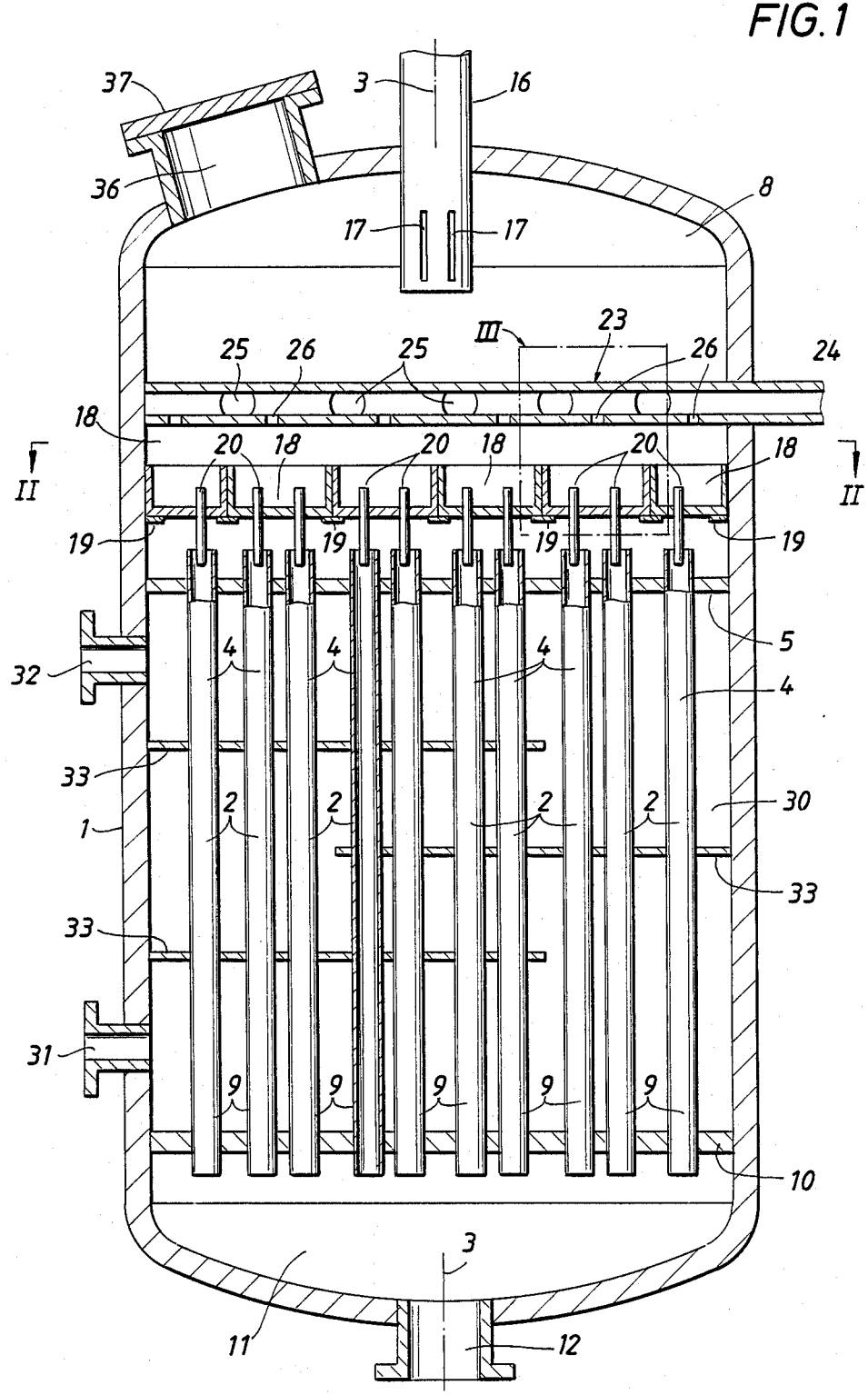
Figure 2:
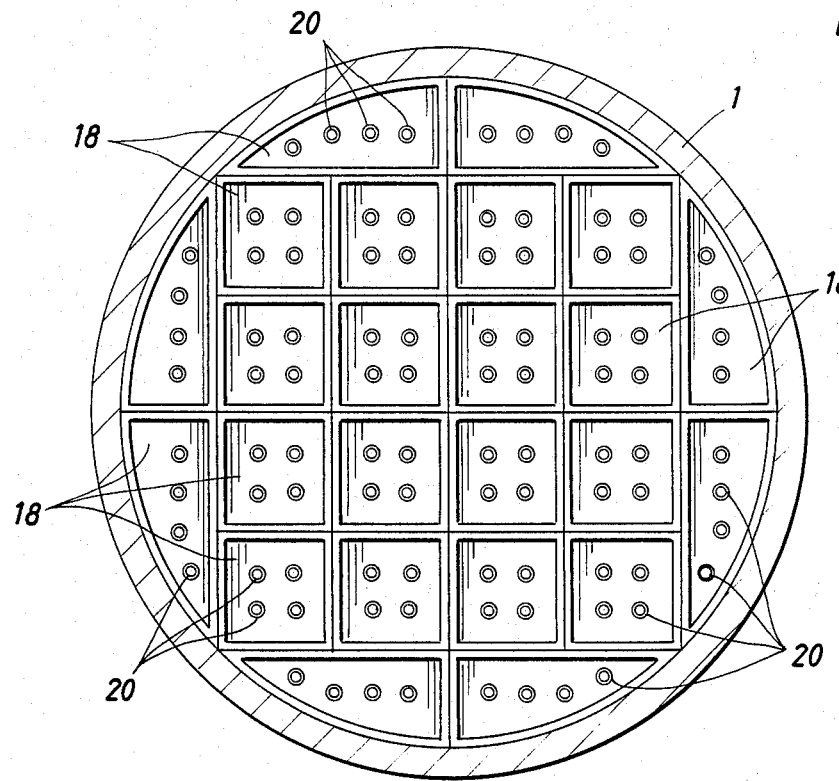
FIG. 2 shows a cross-section of the multitube reactor shown in FIG. 1 along the line II—II.
Figure 3:
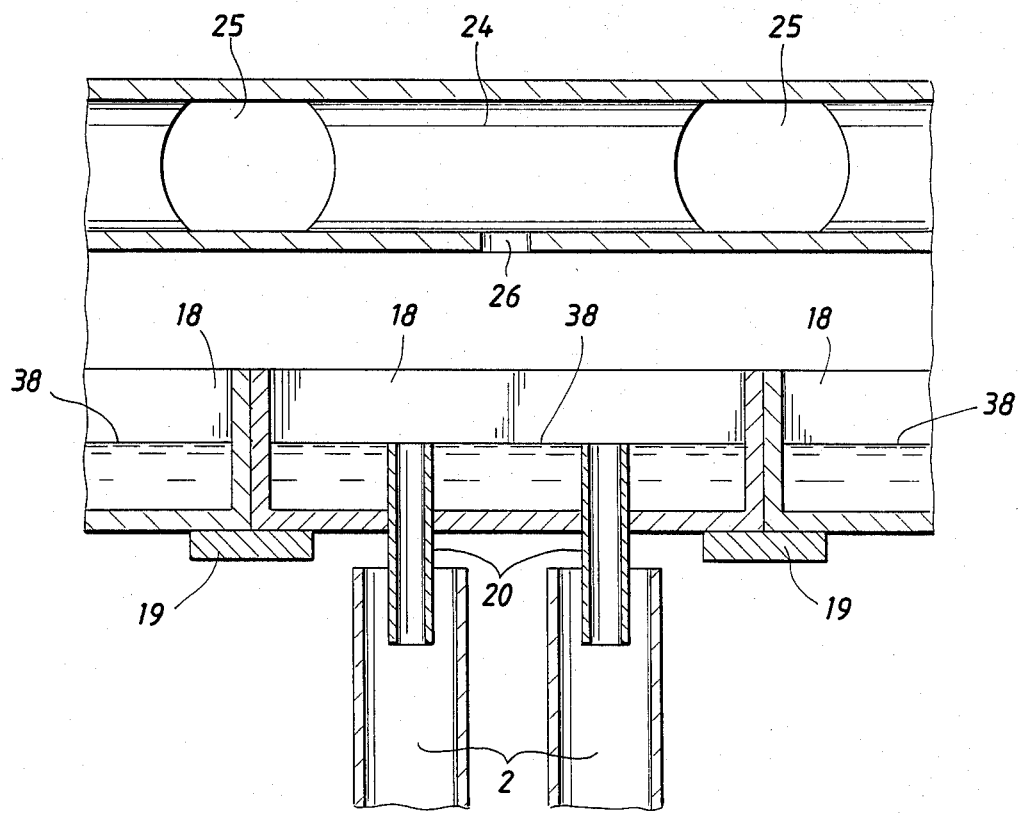
FIG. 3 shows detail III of FIG. 1 drawn to a scale larger than the scale of FIG. 1.

Reference is made to FIGS. 1, 2 and 3. The multitube reactor comprises a normally substantially vertically extending vessel 1, and a plurality of reactor tubes 2 arranged in the vessel 1 parallel to the central longitudinal axis 3 of the vessel 1.

The upper ends 4 of the reactor tubes 2 are fixed to upper tube plate 5 which is supported by the inner wall of the vessel 1. In the upper end of the vessel 1, above the upper tube plate 5, there is a fluid inlet chamber 8 which is in fluid communication with the upper ends 4 of the reactor tubes 2. The lower ends 9 of the reactor tubes 2 are fixed to lower tube plate 10 which is supported by the inner wall of the vessel 1. In the lower end of the vessel 1, below the lower tube plate 10, there is an effluent collecting chamber 11 which is in fluid communication with the lower ends 9 of the reactor tubes 2.

In the effluent collecting chamber 11 there is arranged an effluent outlet 12 provided with means (not shown) allowing or preventing effluent leaving the effluent collecting chamber 11.

In the fluid inlet chamber 8 there is arranged a gas inlet 16 having openings 17 for introducing gas into the fluid inlet chamber 8. Furthermore, there is arranged in the fluid inlet chamber 8 a liquid distributor which includes a plurality of adjacent, substantially horizontal trays 18 having flat bottoms and raised edges. The trays 18 are arranged on support elements 19 supported by the inner wall of the vessel 1. During normal operation liquid collected in the trays 18 and gas can flow into the upper ends 4 of the reactor tubes 2 through downcomers 20 arranged in the bottoms of the trays 18.

It is noted that for clarity in FIG. 2 not all trays and downcomers have been referred to with a reference numeral.

In order to supply liquid to the trays 18, there is arranged in the fluid inlet chamber 8 liquid supply means 23 comprising a main conduit 24 extending through the wall of the vessel 1 and a plurality of secondary conduits 25 extending substantially perpendicular to the main conduit 24 and being in fluid communication with the main conduit 24. The main conduit 24 and the secondary conduits 25 are provided with outlet openings 26 arranged above the trays 18.

The outlet openings 26 are not positioned above a downcomer 20, and they are so dimensioned that, during normal operation, the trays 18 are supplied with the required amounts of liquid such that the reactor tubes 2 receive substantially equal amounts of liquid via downcomers 20.

The part of the vessel between the upper tube plate 5 and the lower tube plate 10 defines a heat-exchange fluid outlet 32 and baffle-plates 33. The reactor tubes 2 are so joined to the upper and lower tube plates 5 and 10 that there is no fluid communication possible between the heat-exchange chamber 30 and the fluid inlet chamber 8, and between the heat-exchange chamber 30 and the effluent collecting chamber 11.

The vessel is provided with a flanged manhole 36 closed by means of a cover 37 bolted thereto.

During normal operation, the reactor tubes 2 are filled with catalyst particles (not shown), supported in the reactor tubes 2 by conventional catalyst support means (not shown) arranged in the lower ends 9 of the reactor tubes 2.

To carry out the process of catalytic conversion of synthesis gas, comprising hydrogen and carbon monoxide, into middle distillates, synthesis gas is introduced in the fluid inlet chamber 8 via the gas inlet 16 at a pressure in the range of from 2 MPa to 4 MPa and at a temperature in the range of from 200° C. to 250° C. The synthesis gas is allowed to enter the catalyst filled reactor tubes 2 through the downcomers 20, and to pass through the reactor tubes 2 where the conversion to middle distillates takes place. The effluents are collected in the effluent collecting chamber 11 and removed therefrom via effluent outlet 12.

To remove the heat of reaction cooling fluid is introduced in the heat-exchange chamber 30 via heat-exchange fluid inlet 31, is passed along the outer surfaces of the reactor tubes 2 and is removed therefrom via heat-exchange fluid outlet 32.

In order to distribute the heat of reaction generated during the catalytic conversion uniformly over the cross-sections of the reactor tubes 2 and to improve heat-transfer from the interiors of the reactor tubes 2 to the inner surfaces of the walls of the reactor tubes 2 a heat-transfer liquid, for example part of the liquid effluent, preferably after being filtered, is introduced into the upper ends 4 of the reactor tubes 2 and allowed to pass therethrough.

The heat-transfer liquid is introduced in the fluid inlet chamber 8 via the main conduit 24 and the secondary conduits 25, and is supplied to the trays 18 through the outlet openings 26 arranged in said conduits. The heat-transfer liquid is collected in the trays 18 until the trays 18 are filled to the liquid levels 38 (see FIG. 3) and then the liquid flows over the upper ends of the downcomers 20 and through the downcomers 20 into the reactor tubes 2. The liquid is collected in the effluent collecting chamber 11 and removed therefrom via effluent outlet 12.

To avoid overheated reactor tubes in the multitube reactor and to obtain similar temperature distributions in the reactor tubes, the outlets 26 should be so dimensioned that each tray 18 receives about the same amount of heat-transfer liquid per reactor tube 2 with which the tray 18 is in communication. In addition, the openings 26 should be positioned in between the downcomers 20 to avoid that a large part of the heat-transfer liquid flows directly into one downcomer.

An advantage of the multitube reactor is that deposits in the liquid can precipitate to the bottom of the tray so that fouling of the catalyst particles in the reactor tubes is avoided.

A further advantage is that the trays can easily be removed from the reactor or placed into the reactor through the manhold.

The liquid level in a tray, and consequently the amounts of liquid flowing into the reactor tubes which are in communication with that tray are only slightly affected by the tilt of the multitube reactor.

The preferred number of trays can be in the range of from about 15 to about 30.

Instead of being supported by support elements 19 (see FIG. 1), the trays 18 can also lie on the upper tube plate 5.

The outer diameter of the downcomer should be about 10 mm smaller than the inner diameter of a reactor tube, and the downcomer extends about 50 to 100 mm above the flat bottom of the tray and about 20 to 100 mm below the bottom.

If required heat transfer liquid can be supplied to a tray through more than one opening, for example three or four.

Figure 4A:
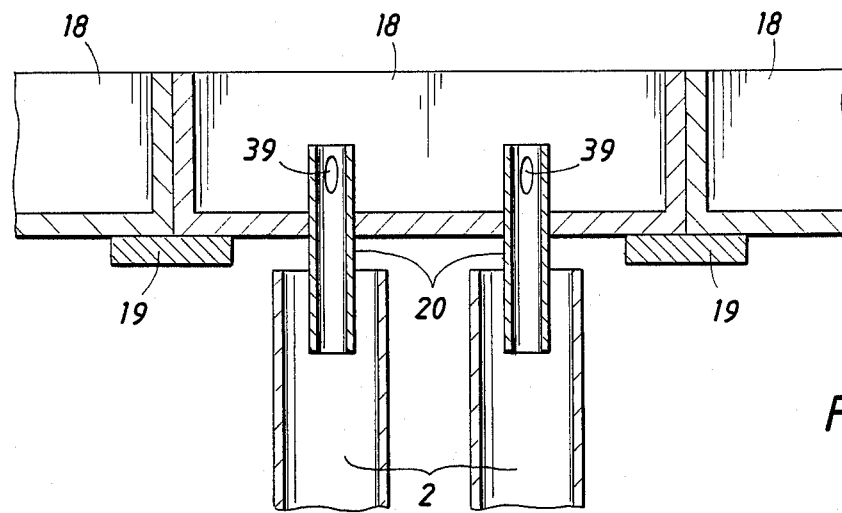
FIGS. 4a and 4b show alternatives for the inlet of the downcomers shown in FIG. 3.
Figure 4B:
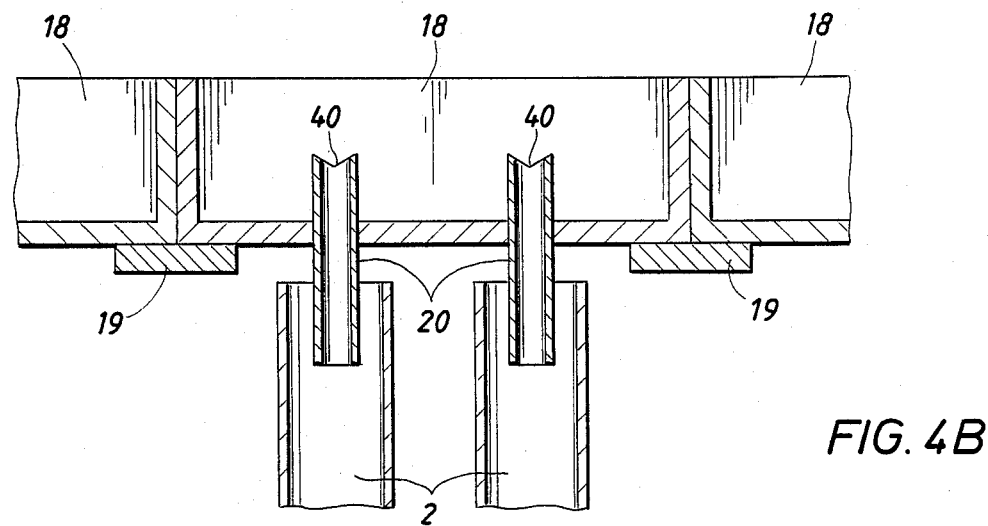

Instead of openings 26, the conduits 24 and 25 can be provided with nozzles (not shown). The nozzles can be arranged in such a manner that their outlet openings are just below the liquid level present in the trays during normal operation to avoid splashing liquid in the trays.

Where more precise closing of heat-transfer liquid to the downcomers 20 is required, the downcomers 20 can be provided with feed holes 39 near the upper ends of the downcomers 20 (see FIG. 4A) or with indentations 40 at their upper ends (see FIG. 4B). If required the downcomers can be provided with both feed holes and indentations.

Figure 5:
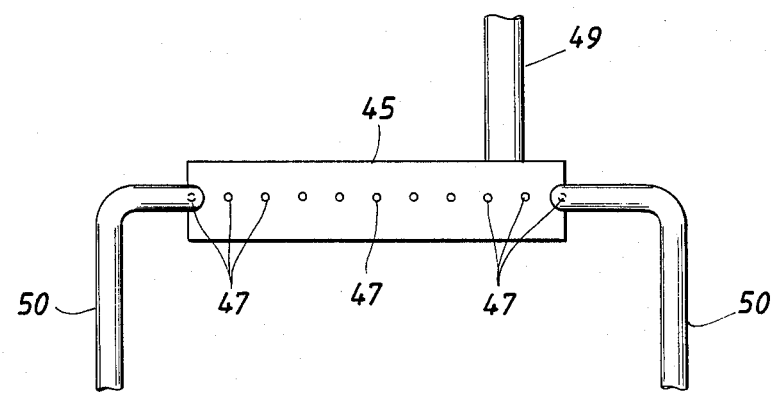
FIG. 5 shows an alternative liquid supply means.

Instead of liquid supply means shown in FIG. 1, the multitube reactor can be provided with liquid supply means comprising a liquid distributor head 45 (see FIG. 5), with outlet openings 47, a supply conduit 49 and a plurality of liquid conduits 50 for transporting liquid from the outlet openings 47 to the trays (not shown in FIG. 5). For clarity only two liquid conduits 50 are shown in FIG. 5.

During normal operation liquid is supplied to the trays by feeding liquid to the supply conduit 49, allowing the liquid to enter the liquid distributor head 45, to leave the head 45 via the outlet openings 47 and to flow to the trays through the liquid conduits 50.

To avoid splashing liquid into the trays, the outlet openings of the liquid conduits 50 can be arranged in the trays just below the liquid level present in the trays during normal operation.

The openings 47 of the liquid distributor head 45 should be so selected that the trays receive about equal amounts of fluid per reactor tube with which the tray is in fluid communication.

The liquid supply means can be provided with one liquid conduit 50 per tray, or, if required, more than one, for example two or three.

The multitube reactor can also be used for catalytic conversion of liquids, for example hydrodemetallization or hydrodesulphurization, wherein a metal-containing or sulphur-containing hydrocarbon liquid is supplied to the reactor tubes via the liquid supply means and the trays and wherein hydrogen is supplied via the gas inlet 16. For these processes, the hydrocarbon liquid is the heat-transfer liquid.

When the multitube reactor is used in an endothermic process, the heat-exchange fluid which is passed along the external surfaces of the reactor tubes may comprise for example steam or hot oil.

The invention can also be used to convert catalytically a gas and a liquid.

What is claimed is:

1. An apparatus for performing a process for catalytic conversion in a multitube reactor, which reactor comprises a normally substantially vertically extending vessel having a longitudinally extending axis, a plurality of reactor tubes arranged in the vessel substantially parallel to said central longitudinal axis, the reactor tubes having upper ends fixed to an upper tube plate and in fluid communication with a fluid inlet chamber above the upper tube plate, the reactor tubes having lower ends fixed to a lower tube plate and in fluid communication with an effluent collecting chamber below the lower tube plate, a means for passing heat-exchange fluid along the outer surfaces of the reactor tubes, an effluent outlet arranged in the effluent collecting chamber, a gas inlet arranged in the fluid inlet chamber, a liquid distributor in the fluid inlet chamber which includes a plurality of adjacent, removable, substantially horizontal trays having flat bottoms and raised edges, which substantially horizontal trays are provided with a plurality of downcomers extending through the bottom of the tray in fluid communication with the upper ends of the reactor tubes, and a liquid supply means for supplying liquid to the substantially horizontal trays.

2. The apparatus of claim 1 wherein at least one downcomer is provided with a means of defining a feed hole near the upper end of the downcomer.

3. The apparatus of claim 2 wherein at least one downcomer is provided with indentations at the upper end of the downcomer.

4. The apparatus of claim 3 wherein the liquid supply means comprise a plurality of conduits having outlet openings arranged above the substantially horizontal trays.

5. The apparatus of claim 3 wherein the liquid supply means comprise a liquid distributor head having outlet openings and liquid conduits for transporting liquid from the outlet openings to the substantially horizontal trays.

6. The apparatus of claim 4 wherein the outlet openings are selected such that, during normal operation, each tray receives about the same amount of fluid per reactor tube with which the tray is in fluid commuinication.

7. The apparatus of claim 1 wherein the number of substantially horizontal trays which are in fluid communication with the upper ends of the reactor tubes is about 15 to about 30.

* * * * *